(12) United States Patent
Rogers (10) Patent No.: US 6,225,067 B1
(45) Date of Patent: May 1, 2001

(54) METHODS AND DEVICES FOR PERFORMING ANALYSIS OF A NUCLEIC ACID SAMPLE

(75) Inventor: Charles H. Rogers, Halifax, MA (US)

(73) Assignee: bioMérieux, Inc., Hazelwood, MO (US)

( * ) Notice: Subject to any disclaimer, the term of this patent is extended or adjusted under 35 U.S.C. 154(b) by 0 days.

(21) Appl. No.: 09/443,027

(22) Filed: Nov. 18, 1999

Related U.S. Application Data (62) Division of application No. 09/291,566, filed on Apr. 13, 1999.

(51) Int. Cl.⁷ .................................................... C12Q 1/68
(52) U.S. Cl. ......................... 435/6; 435/91.2; 536/23.1
(58) Field of Search ..................... 435/6, 91.2; 536/23.1

(56) References Cited

U.S. PATENT DOCUMENTS

| | | | |
|---|---|---|---|
| 4,213,893 | 7/1980 | Carrico et al. | 260/112.5 R |
| 4,411,955 | 10/1983 | Mondt et al. | 428/413 |
| 4,486,539 | 12/1984 | Ranki et al. | 436/504 |
| 4,563,419 | 1/1986 | Ranki et al. | 435/6 |
| 4,683,195 | 7/1987 | Mullis | 435/6 |
| 4,683,202 | 7/1987 | Mullis | 435/91 |
| 4,851,330 | 7/1989 | Kohne | 435/6 |
| 4,882,269 | 11/1989 | Schneider et al. | 435/6 |
| 5,079,342 | 1/1992 | Alizon et al. | 530/324 |
| 5,202,231 | 4/1993 | Drmanac et al. | 435/6 |
| 5,213,961 | 5/1993 | Bunn et al. | 435/6 |
| 5,310,651 | 5/1994 | Alizon et al. | 435/6 |
| 5,399,491 | 3/1995 | Kacian et al. | 435/91.21 |
| 5,409,818 | 4/1995 | Davey et al. | 435/91.21 |
| 5,437,900 | 8/1995 | Kuzowski | 428/36.1 |
| 5,445,934 | 8/1995 | Foder et al. | 435/6 |
| 5,457,027 | 10/1995 | Nadeau et al. | 435/6 |
| 5,476,744 | 12/1995 | Wang et al. | 435/91.2 |
| 5,512,493 | 4/1996 | Mathis et al. | 436/537 |
| 5,545,527 | 8/1996 | Stevens et al. | 435/6 |
| 5,547,842 | 8/1996 | Hogan et al. | 435/6 |
| 5,559,662 | 9/1996 | Happ et al. | 361/104 |
| 5,589,585 | 12/1996 | Mabilat et al. | 536/24.32 |
| 5,614,388 | 3/1997 | Picone et al. | 435/91.2 |
| 5,631,147 | 5/1997 | Lohman et al. | 435/91.2 |
| 5,643,723 | 7/1997 | Persing et al. | 435/6 |
| 5,648,211 | 7/1997 | Fraiser et al. | 435/6 |
| 5,700,637 | 12/1997 | Southern | 435/6 |
| 5,703,217 | 12/1997 | Mabilat et al. | 536/23.1 |
| 5,705,365 | 1/1998 | Ryder et al. | 435/91.1 |
| 5,710,628 | 1/1998 | Waterhouse et al. | |
| 5,744,311 | 4/1998 | Fraiser et al. | 435/6 |
| 5,786,182 | 7/1998 | Catanzariti et al. | 435/91.1 |
| 5,792,607 | 8/1998 | Backman et al. | 435/6 |
| 5,795,722 | 8/1998 | Lacroix et al. | 435/6 |
| 5,807,522 | 9/1998 | Brown et al. | 422/50 |
| 5,837,832 | * 11/1998 | Chee et al. | 536/22.1 |
| 5,849,901 | 12/1998 | Mabilat et al. | 536/23.7 |

FOREIGN PATENT DOCUMENTS

| | | | |
|---|---|---|---|
| 0 875 584 A2 | * 5/1998 | (EP) | C12Q/1/68 |
| WO 96/18892 | 6/1996 | (WO) . | |

OTHER PUBLICATIONS

1. Extensive polyhmorphisms observed in HIV–1 clade B protease gene using high density oligonucleotide arrays, Michael J. Kozal, et al., Nature Medicine, vol. 2, No. 7, pp. 753–759, (Jul. 1996).

Lauricella–Lefebvre et al., "High rate of Multiple Genital HPV Infections Detected by DNA Hybridization" Jounal of Medical Virology vol.36, pp.265–270, 1992.*

* cited by examiner

*Primary Examiner*—John S. Brusca
*Assistant Examiner*—Jeffrey S. Lundgren
(74) *Attorney, Agent, or Firm*—McDonnell Boehnen Hulbert & Berghoff

(57) ABSTRACT

An automated instrument and method for nucleic acid analysis is provided. The automated instrument is an integrated system including a sample processing station, a first reaction module, a second reaction module, a detection module and a control module for performing homogenous screening of broad specificity and multi-detection reactions on a nucleic acid test sample. The nucleic acid analysis performed in the instrument includes the steps of conducting a first test reaction using a low detection format, and if necessary, a selected second test reaction using a high detection format, detecting signals generated from the test reactions and processing signal data in a control module.

10 Claims, 6 Drawing Sheets

SEQUENCE LISTING

```
<160> NUMBER OF SEQ ID NOS: 5

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide T3-MI

<400> SEQUENCE: 1
aattaaccct cactaaaggg aacacgtggg tgatctgccc tgca                 44

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide T7-M2

<400> SEQUENCE: 2
gtaatacgac tcactatagg gcttgtggcc ggacaccctc tca                  43

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide 33f
```

-continued

```
<400> SEQUENCE: 3
tcacagcccg ataacaccaa c                                                    21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide 2288r

<400> SEQUENCE: 4
ggccgatcaa cccgaatcag c                                                    21

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Detection
      probe

<400> SEQUENCE: 5
gatgagcccg cggcctatca gcttgttggt                                           30
```

METHODS AND DEVICES FOR PERFORMING ANALYSIS OF A NUCLEIC ACID SAMPLE

This is a divisional of Ser. No. 09/291,566, filed Apr. 13, 1999.

BACKGROUND OF THE INVENTION

1. Technical Field

The field of the invention relates to methods and devices for conducting analytical or biological sample testing, such as, for example, for the purpose of identification of microorganisms or viruses in a test sample, and/or the susceptibility or resistance of the microorganisms or viruses to drugs. The invention is particularly related to the field of methods and devices for detection and analysis of nucleic acids present in a biological test sample.

2. Technical Review

Nucleic acid examination is a continually emerging area for test sample analysis including investigating genetic sequence and expression. Initially, a test sample from a human patient or other source is isolated and target nucleic acids in the sample are amplified to increase the number of copies to allow the test sample to be analyzed. The copies of target sequences are then hybridized to one or more complementary oligonucleotide probes in solution or in combination with a solid support incorporating complementary probes to form a hybridization complex. A detector probe may also be hybridized to the target sequences under some reactions. Detection and identification of the hybridization product is achieved when a signal is generated from the hybridization complex formed. By amplifying nucleic acid sequences, information about the presence or absence of microorganisms is obtained from the sample without resorting to culturing microorganisms.

An amplification method is described in U.S. Pat. No. 4,683,195 (Mullis) and U.S. Pat. No. 4,683,202 (Mullis), in which a polymerase chain reaction (PCR) utilizes DNA polymerase, complementary primer molecules and repeated cycles of thermal reactions to exponentially replicate target nucleic acid molecules. U.S. Pat. No. 5,792,607 (Backman) describes amplification methods referred to as ligase chain reactions (LCR). U.S. Pat. No. 5,744,311 (Fraiser); U.S. Pat. No. 5,648,211 (Fraiser) and U.S. Pat. No. 5,631,147 (Lohman), describe isothermal amplification systems based on strand displacement amplification (SDA). See also, Walker, et al., *Nuc. Acids. Res.* 20, 1691–1696 (1992) U.S. Pat. No. 5,437,900 (Burg) and EP 373 960 (Gingeras), describe isothermal amplification. Still other nucleic acid amplification methods are described in U.S. Pat. No. 5,399,491 (Kacian) and U.S. Pat. No. 5,409,818 (Davey). Each and all references noted above are incorporated herein by reference together with all other patents and literature references cited herein.

Hybridization techniques have been described for example, in U.S. Pat. No. 4,563,419 (Ranki) and U.S. Pat. No. 4,851,330 (Kohne) and in Dunn, et al., *Cell* 12, pp. 23–26 (1978) among many other publications. Various modifications to the hybridization reactions are known in the art including in solution hybridization or to capture probes on a solid support in one or more reaction steps.

Detection methods described in U.S. Pat. No. 4,486,539 (Kourlisky); U.S. Pat. No. 4,411,955 (Ward) 4,882,269 (Schneider) and U.S. Pat. No. 4,213,893 (Carrico), illustrate preparation of labeled detection probes for detecting specific nucleic acid sequences. Detectable labels have been conjugated, directly or indirectly through linker arms on either the base, sugar or phosphate moiety of one or more specific oligonucleotides. Labels known in the art include fluorochromes, radioisotopes, dyes, enzymes such as alkaline phosphatase, and luminescent or chemiluminescent molecules. The detector probes may bind to the amplified nucleic acid reaction products or amplicons. The amount of signal detected from the labeled detector probes after hybridization to amplicons reflects the presence or absence of amplicons and therefore of one or more selected target nucleic acid in the original test sample.

In general, amplifying known starting quantities of an internal control in a sample, then hybridizing with detector probes having an opposite sequence or sense to form a complex with the internal control amplicons and finally detecting signal generated provides one method to permit the qualitative and quantitative determination of target nucleic acids in a test sample.

Quantitative methods to determine the amount of target present in the test sample are described in U.S. Pat. No. 5,213,961 (Bunn); U.S. Pat. No. 5,476,774 (Wang); U.S. Pat. No. 5,705,365 (Ryder) and U.S. Pat. No. 5,457,027 (Nadeau).

Nucleic acid detection kits are commercially available and employ some of the abovereferenced amplification, hybridization, labeling detection and quantitation techniques. For example, an HIV assay which detects amplified nucleic acid is described in U.S Pat. No. 5,559,662 (Respess) and Gratzi, et al, *J Virol. Methods* 66, pp. 269–292 (1997). Kits which achieve such amplification of HIV nucleic acids include the Chiron QUANTIPLEX Branched DNA and Organon Teknika NASBA-QT.

A test kit for M. tuberculosis is described in U.S. Pat. No. 5,643,723 (Persing) and nucleic acids for mycobacteria testing are described in U.S. Pat. No. 5,589,585 (Mabilat); U.S. Pat. No. 5,702,317 (Mabilat) and U.S. Pat. No. 5,849,901 (Mabilat).

Nucleic acid sequence analysis can be divided into two different categories: limited detection or low detection formats, and multi-detection or high detection formats. The distinction is the number of specific data signals or responses that can be obtained from the formats.

EP 0 875 584 describes an instrument that uses a low detection formats. A single type of fluorescent label bound to a detection probe can be measured to determine the presence of complementary nucleic acids in the test sample. By sequentially using this technique, the instrument has been shown to be able to measure at least two specific targets in a test sample. Alternatively, multiple labels can be measured in a screening assay simultaneously (eg; fluorescent or luminescent labels with different emission properties). However for practical reasons, the number of target analytes that can be measured in a screening assay remains less than ten. These techniques are considered included in the category of low detection formats.

The design or selection of a test panel in a low detection format will be determined in part by customer need, by disease incidence in a particular location, by the prevalence of co-infection of microorganisms and/or viruses and environmental conditions to name but a few. While low resolution or low detection formats such as nucleic acid detection kits noted above are useful in detecting the presence of a conserved or limited number of target sequences, these tests have been less effective for obtaining higher levels of data or detail about target nucleic acids which are needed for analysis of a particular variant, its drug susceptibility or presence of a mutation.

The second category of analytical methods is a multi-detection or high detection format. These methods are capable of providing more detailed information about the target amplicons. An example of this is the reverse dot-blot technique, wherein nucleic acids are hybridized to multiple complementary probes immobilized on a matrix. After staining, the multiple sections that become stained indicate the presence of complementary target(s). Another technique provides a light-directed, spatially addressable matrix or array on which is deposited numerous oligonucleotides.

Recent advances in large scale genetic analysis utilize oligonucleotides assembled as multi-detection arrays by microfabrication techniques. Synthesis and methods of these arrays are described in U.S. Pat. No. 5,700,637 (Southern); U.S. Pat. No. 5,445,934 (Fodor); U.S. Pat. No. 5,807,522 (Brown); U.S. Pat. No. 5,202,231 (Drmanac) and U.S. Pat. No. 5,837,832 (Chee). The arrays allow hybridization reactions in which the immobilized oligonucleotides are explored by labeled probes or labeled amplicons for identification of variants or mutations such as single or multiple base substitutions. In an example of an application, multi-detection arrays for detection of human immunodeficiency viruses are described in Fodor, Stephen et al., "Light-Directed, Spatially Addressable Parallel Chemical Synthesis", *Science*, Vol. 251 pp.767–773 (1991).

While both low and high detection formats have been used in analytical and diagnostic tests, they have different capacities. Low detection formats have the advantage of simplicity, relatively low cost and capacity to answer specific questions regarding a sample, e.g., does this sample contain nucleic acids typically from a region of the HIV virus. The high detection formats are more expensive but can provide even more data or information for analysis, e.g,. does this sample of HIV nucleic acids have mutations from the wild-type sequence, and if so, what are they? Because of their expense, multi-detection or high detection formats have not been viewed as a cost effective means for routine screening tests. Thus commercial tests typically have been provided as limited or low detection formats mainly to confirm a medical hypothesis as illustrated in FIG. 1.

Figure 1:
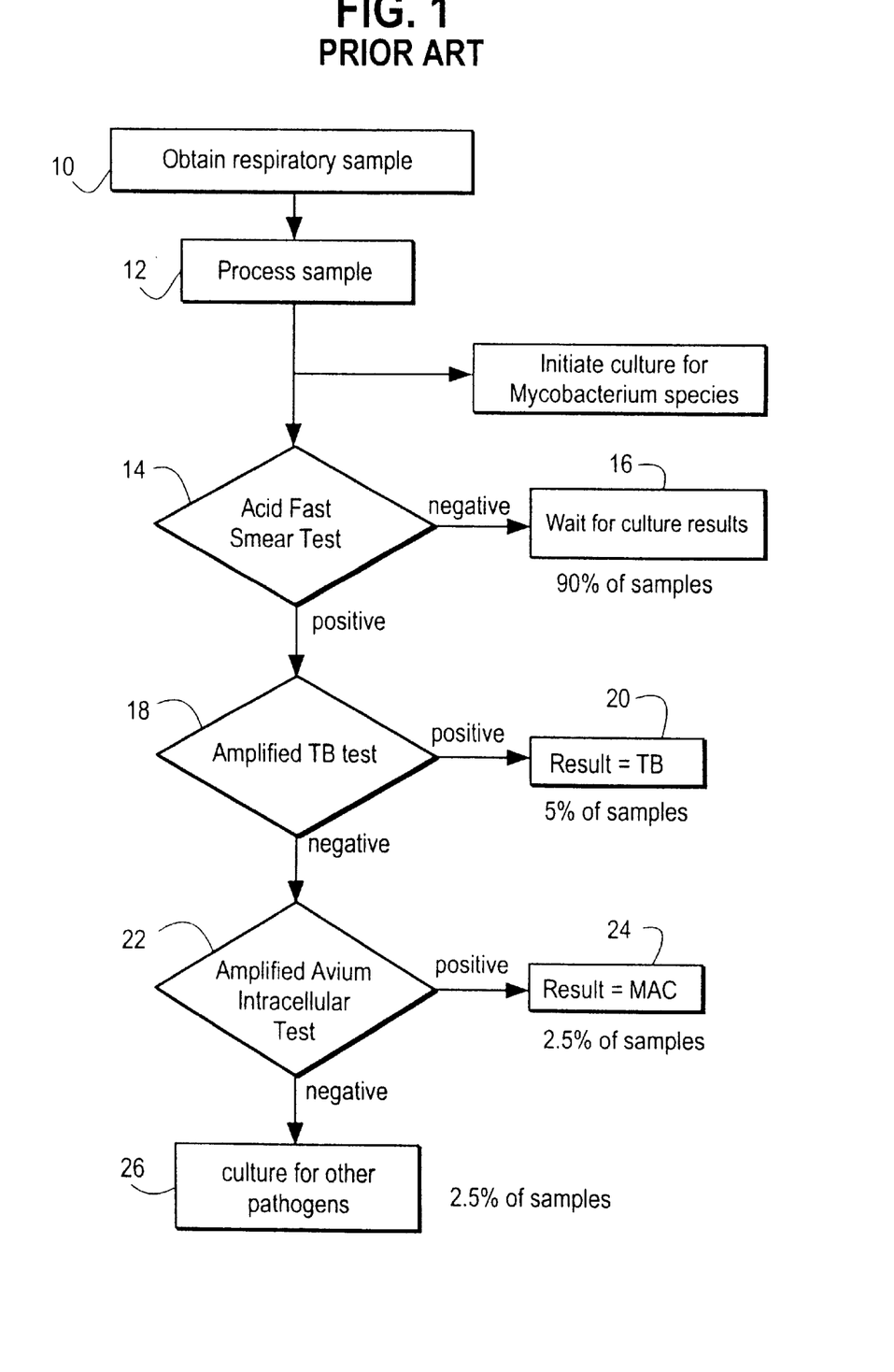
FIG. 1 is an illustration of a prior art method for conducting a plurality of tests on a human sample, in flow chart form, initiated with a tentative hypothesis of the infectious agent in the sample.

In FIG. 1, a hypothesis that the patient is suffering from tuberculosis begins the testing process. A respiratory sample is obtained from a patient's sputum at step 10. The sample is processed at step 12 to prepare the organism for culture. The sample is then divided and one part used to culture the organisms. At step 14, a second portion of the sample is subjected to an Acid Fast Smear Test. If the test result from the Acid Fast Smear Test is negative, the physician must wait for the results of the culture as indicated at 16. If positive, the clinician processes the sample again, and is subjected to an amplified species specific TB test performed at 18. At step 22, an amplified Avium Intracellular test may be a third test performed on the test sample to identify the sample. If the test result at step 22 is negative, the test sample or a new second sample may be subjected to a subsequent test reaction or cultures to determine if pathogens are present in the sample.

FIG. 1 is a typical example of a low cost test known in the prior art, the Acid Fast "Smear" (step 14) is used to reject 90% of the test samples suspected of including Mycobacteria which are negative. Subsequent tests could be justified for use on the 10% of the samples that are positive, but even if test costs are low, the expense of labor and handling samples may not be justified if they must be used for all test samples.

There remains a need for instruments and automated methods that not only include but also proceed beyond limited detection screening for nucleic acid analysis. The availability of such an instrument will provide valuable information and data in, for example, identifying genetic disorders that may produce physiological effects which mimic or overlap other genetic disorders. There is also a need for an instrument system that can provide integrated test stations and data to determine the resistance of microorganisms to an available drug, for deciding appropriate therapy. Furthermore, such a system should aim for minimum manipulation by the researcher or clinician, especially those steps involving sample preparation, amplification, and detection. It should preferably be applicable as a tool to improve monitoring, data collecting, sequencing and genotyping of nucleic acids while limiting the risk of contamination between each test or step. The system should also be accurate, highly sensitive and available to the consumer at reasonable costs.

SUMMARY OF THE INVENTION

The present invention provides a method and instrument system for automatically controlling the choice of when to use a multi or high detection format for further nucleic acid analysis. These methods include the steps of detecting target amplicons produced by at least one amplification reaction in a limited detection or low detection format and then using a control algorithm in an integrated system incorporating data or signals from the low detection format to determine whether the target amplicons are analyzed with use and cost of a high detection format. The system utilizes output data from a first test reaction as the input data for the control algorithm and the selection of a high detection format.

A further object of the invention is to provide one or more signal data from one or more first test reaction(s) for qualitative and/or quantitative analysis. In a first test reaction, an amplified target nucleic acid from a test sample along with an amplified internal control sequence preferably having a known concentration are subjected to hybridization and detection reactions to generate signal data. The signals obtained are supplied to a control module, processed and compared with threshold level signals specific for either target/test sample or internal control amplicons. The combination of signals are applied to an algorithm which determines whether target amplicons are transferred automatically to another station of the instrument for further testing. If applicable, a second test reaction using one or more selected high detection format(s) generates further analytical data for the target amplicon(s) such as the identification of a variant, a mutation in nucleic acid sequence, drug susceptibility or resistance of the microorganism or virus. The analysis of the second test reactions includes hybridization of the amplicons in at least one high detection format.

In a preferred embodiment, the present invention provides an instrument for nucleic acid analysis which is comprised of a sample processing station preferably including nucleic acid amplification capability, first and second reaction stations or modules and appropriate detection stations, with each station directed by a control module. A fluidic passageway or preferably fluidic transfer means is also provided and which optionally connects amplicons from the first test reaction station with the second test reaction station or module. Each station may communicate with another under regulation of the control module. The control module integrates data obtained from the first reaction station and corresponding detection station in a feedback loop to terminate the process or initiate a second reaction in the second test reaction station followed by detection and signal analysis.

In another embodiment of the present invention, the system is a modular automated instrument system that integrates the methods of sample processing, amplification, hybridization, and detection and the system is further capable of analyzing whether additional data collection tests on a test sample should be performed and thereafter performing such additional data collection assays.

An objective of the present invention is to use low cost technologies, i.e., limited detection formats in an automated system, to "screen" a target nucleic acid sequence in a sample in determining the need for further analysis. The screening step should have high sensitivity but broad specificity to detect as "positive" at least all the samples that can be further analyzed by the high detection formats of the system.

In another aspect, a comprehensive instrument system is provided for fully determining target nucleic acid sequences by utilizing different reaction technologies, i.e., hybridization and/or detection. In a preferred embodiment a screening test utilizing a homogenous solution hybridization reaction is performed and an array or matrix hybridization is utilized for multi-detection analysis. In another objective a screening analysis may be provided without a prior amplification protocol in order to provide signal data to the control module for purpose of defining the need to perform one or more matrix based hybridization assays.

The systems of the invention can be used, e.g., in microbiology, virology, food investigations, water testing, diagnostics of human and animal diseases, and analytical research use. Suitable biological or test sample materials include animal, human or plant cells or tissue, blood, urine, feces, nasal and urethral mucous. Further, the invention may be used in industrial applications such as food processing, contamination control or pharmaceutical research.

The present invention overcomes the numerous limitations inherent in the attempts of other methodologies and thus, provides cost effective means for accurately and more completely identifying nucleic acids in a biological or test sample. More particularly, in one aspect of the invention critical data and information is provided for the purpose of disease detection, identification for drug resistance and therapy.

BRIEF DESCRIPTION OF THE DRAWINGS

Representative preferred and alternative embodiments of the invention will be described below in conjunction with the appended drawing figures, where like reference numerals refer to like elements in the various views, and in which.

DETAILED DESCRIPTION OF THE INVENTION

Limited or low detection formats include the hybridization and detection methods mentioned above. These may be performed in solution or using capture probes bound to a matrix. Matrixes on which probes have been immobilized include polystyrene-based polymers, nitro-cellulose, sheets of various compositions, beads, micro-titre wells, tubes, glass particles, magnetic particles, natural and synthetic fibers. As used herein, a low detection format, includes less than fifty and preferably at least one to ten oligonucleotide probes having discrete sequences. Each probe contains in part a sequence fully or partially complementary to the amplicons from the test sample and optionally to the internal control. A high detection format, as used herein, includes greater than one hundred and preferably greater than four hundred and most preferably greater than one thousand oligonucleotide probes each having a discrete sequence, bound or immobilized on a suitable matrix. The probes may be applied to the matrix in a high spatial density, for example 400 probes/cm$^2$ to 1000 probes/cm$^2$. Each probe contains in part a sequence filly or partially complementary to a potential target amplicon sequence.

In a preferred embodiment the low detection format is different from the high detection format. For example, the low detection format would include a device for performing a homogenous solution hybridization reaction while the high detection format would include a device for performing a matrix hybridization reaction. Alternatively, a matrix hybridization reaction could be utilized for the low detection format to screen a small number of target amplicons and internal control amplicons.

Figure 2:
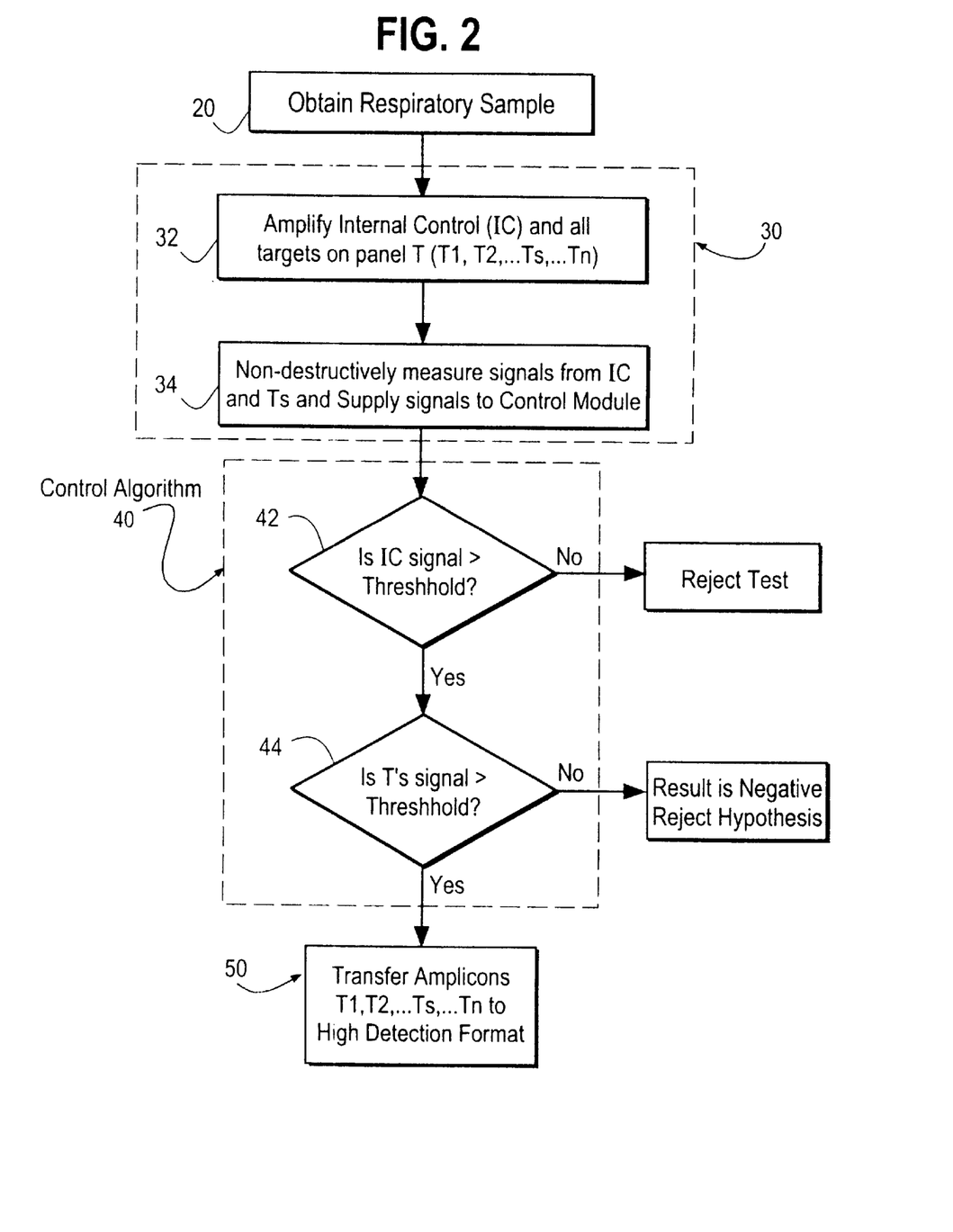
FIG. 2 is an illustration of a method in accordance with the present invention, by which a high detection format is only performed if a control algorithm processing signal from a low detection format indicates that a high detection format is justified.

Referring now to FIG. 2, a preferred embodiment provides method and device for automatically directing continuation of analysis and controlling the selection of a high detection format is shown in the flow-chart. The method involves the step of detecting amplicons produced by an amplification reaction of target nucleic acids in a test sample using a low detection format (shown generally by step 30) and using a control algorithm 40 to determine the use of one or more high detection formats. The preferred embodiment may incorporate a single amplification step for complete analysis of the nucleic acids in the test sample. Accordingly, the sample is submitted to an initial number of first hybridization reactions for purpose of performing a screening analysis having broad specificity and a cost-effective choice of the technology to be used for the analysis is determined by use of the automatic control algorithm 40 with appropriate data input. The output data from a low detection format is the input data for a selected high detection format (step 50).

The method of FIG. 2 makes it possible to use low cost technology, i.e., a low detection format in step 30, to screen a sample. Use of such an approach allows target amplicons to be utilized throughout sample analysis. If the control algorithm 40 determines that the need of a high detection format 50 is justified, a second analysis 50 is initiated. Data input from a prior test or analysis may also be provided by the user of the system before or at the time of test sample introduction to the device of the present invention.

In the first step 30 of the above methodology (i.e., measuring the target amplicons in a low detection format) nucleic acids are treated or released and preferably amplified in an assay chosen to give a "screening" sensitivity as close to 100% as possible. That is, when a sample is actually positive in any parameter in a chosen screening format, the first assay test reaction will give a positive result.

In a representative embodiment, the first step 30 comprises two separate substeps. The first substep 32 comprises the step of amplifying an internal control sequence and all suspected target nucleic acids in a representative testing panel i.e., respiratory, blood, etc. to generate internal control amplicons and target amplicons, (i.e., T1, T2, . . . Tn). The internal control amplicon is measured as a means to insure that a negative result has not been caused by technical failure. As used herein, internal control sequences are oligonucleotide sequences which are tailored to be unaffected by target nucleic acid sequences, are not substantially similar to any nucleic acid sequences in the sample, and are determinative of a positive amplification process. Generally, an internal control is co-amplified with the target to provide a positive amplification control. The internal control signal may also be utilized in quantitative test sample data analysis.

The second substep 34 comprises the step of measuring the signals from each of the internal control and targets. The equipment used for measuring signals is integrated within the system.

In the second step of the process 40, i.e., implementing the control algorithm, the signals are applied to the control algorithm as illustrated in the dotted-line box 40. The internal control signal is used to indicate if the amplification process is satisfactory. The control algorithm 40 implements the two signals to control whether the sample analysis continues to the next step 50, or not.

In one embodiment, shown in FIG. 2, if the internal control signal is below a predetermined threshold (42), the test is rejected because the amplification reaction did not occur or for other reasons failed to achieve the proper threshold level. If the internal control signal is above the threshold, the algorithm determines (44) whether the screening parameter for one or more targets is greater than a threshold. If it is not, the test result is deemed negative and the hypothesis is rejected. The cost or need of the second step 50 of the analysis is therefore not incurred. Conversely, if the screening parameter is above the threshold (44), the second step 50 in the assay is allowed to proceed.

In a preferred embodiment, the methodology of FIG. 2 is performed in a manner in which the output or result of the first step 30 is used as the input for deciding whether to perform a second step 50 on a selected high detection format. In contrast, further or subsequent tests described in the prior art require separate or repeated access to the sample and in many circumstances the need for further sampling. The prior art tests require sample storage, added handling, and a repeat of processing steps which are avoided by the present invention. Furthermore, in the prior art, human intervention is needed to examine the results of the first test and to decide on subsequent actions. Preferably the test sample is accessed once and only once at the beginning of the process of FIG. 2.

In a preferred embodiment of the present invention, all of the steps 30, 40 and 50 are integrated within an automated analytical instrument to arrive at the final result without human intervention during the process including the performance of the low detection format (step 30). The instrument, in accordance with a preferred embodiment of the invention performs all amplifications for all targets that may be analyzed in the high detection format 50, within the first step 30. The instrument can then direct the sample having sufficient quantities of amplicons to a high detection for a more comprehensive analytical identification.

A preferred embodiment of the high detection format is the Affymetrix GENE CHIP technology, described in U.S. Pat. No. 5,837,832 (Chee). Labeled amplicons derived from nucleic acids from a patient's sample are isolated by standard biochemical techniques then washed over the surface of a high density cartridge (GENE CHIP). Copies of single stranded DNA sequences or probes in the high density cartridge hybridize to complementary labeled amplicons. A laser scanner detects fluorescent signals from known positions on which labeled sequences are hybridized.

A representative preferred embodiment of step 30 in FIG. 2 will now be further described. In the first part of the assay, suspected nucleic acid targets must be processed. During development of the test protocol, conditions involved in the amplification reaction such as probe sequence, primers, conserved sequences, etc. must be identified in view of the parameters to be tested in the panel. In addition, at least one loci must be chosen which has the properties to make it part of the control algorithm, for example, and with reference to FIG. 3, a test of Mycobacterium from a sputum sample, is described in U.S. Pat. No. 5,589,585 (Mabilat); U.S. Pat. No. 5,702,317 (Mabilat), and U.S. Pat. No. 5,849,901 (Mabilat). A conserved or consensus region of the 23S rRNA sequence is chosen as the screening parameter for the low detection format. Amplification of a highly conserved region of the 23S rRNA which can be used for detecting Mycobacterium is performed in a low detection format. Amplification is also performed on DNA of the rpoB gene that is related to resistance to rifampin in Mycobacterium tuberculosis, as indicated in step 32A for use in a high detection format if the screen assay result meets the appropriate threshold. Since there are many more copies of rRNA than DNA per organism, the 23S RNA region is a more reliable indication of the presence of Mycobacterium. As a last requirement, the primers used for the 23S rRNA are used in conjunction with an internal control sequence to generate internal control amplicons so that amplification performance and quantitative analysis can be performed.

In one embodiment, the amplicons from the first step 30 of the test will be transferred to the second step 50, the choice of the screening and detection technology must be compatible with the requirements of the high detection format. This is preferably accomplished by using a homogeneous detection technology for step 32, such as described in U.S. Pat. No. 5,512,493 (Mathis), or "DNA probes" second ed., G. H. Keller and M. M. Manak, Stockton Press, 1993, section 6. Alternately, an energy transfer based hybridization or beacon/detector technology is described in Gionata Leone, et al., "Molecular beacon probes combined with amplification by NASBA enable homogeneous, real-time detection of RNA", *Nucleic Acids Research*, Vol. 26, pp 2150–2155 (1988). The beacons/detectors allow homogeneous detection of a target sequence and are composed of a stem-loop structure in which the loop portion contains the sequence complementary to the amplicons. In the presence of target, the stem of the beacon/detector structure is "opened" and the loop hybridizes to the target. The "open" beacon/detector produces fluorescence that normally is quenched in the "closed" state. According to one embodiment of the present invention, a portion of the beacons/detectors are immobilized onto a solid support using techniques well known in the art. The solid support can be a disposable device including preferably microparticles or magnetic particles. The beacons/detectors should be constructed in such a way that the reaction conditions open the stem structure sequence. The amplicons are brought into contact with the beacons/detectors to thereby allow the stem structure of the beacons/detectors to open and hybridization to the loop structure to occur. See step 32B in FIG. 3. If target amplicons are present the open structure moves the quencher away from the detector molecule allowing the label to be detected. The resulting signal is stored to be used by the control algorithm 40.

The control algorithm for step 40, when used in conjunction with the chosen threshold(s), can effect three different types of processes: (1) qualitative detection of the presence of the expected target; (2) quantitative detection of one or more targets, to be used in conjunction with results of the high detection format, and (3) quantitative detection of one of the several targets, and pre-selection of a specific array of tests for the high detection format assay 50.

Figure 3:
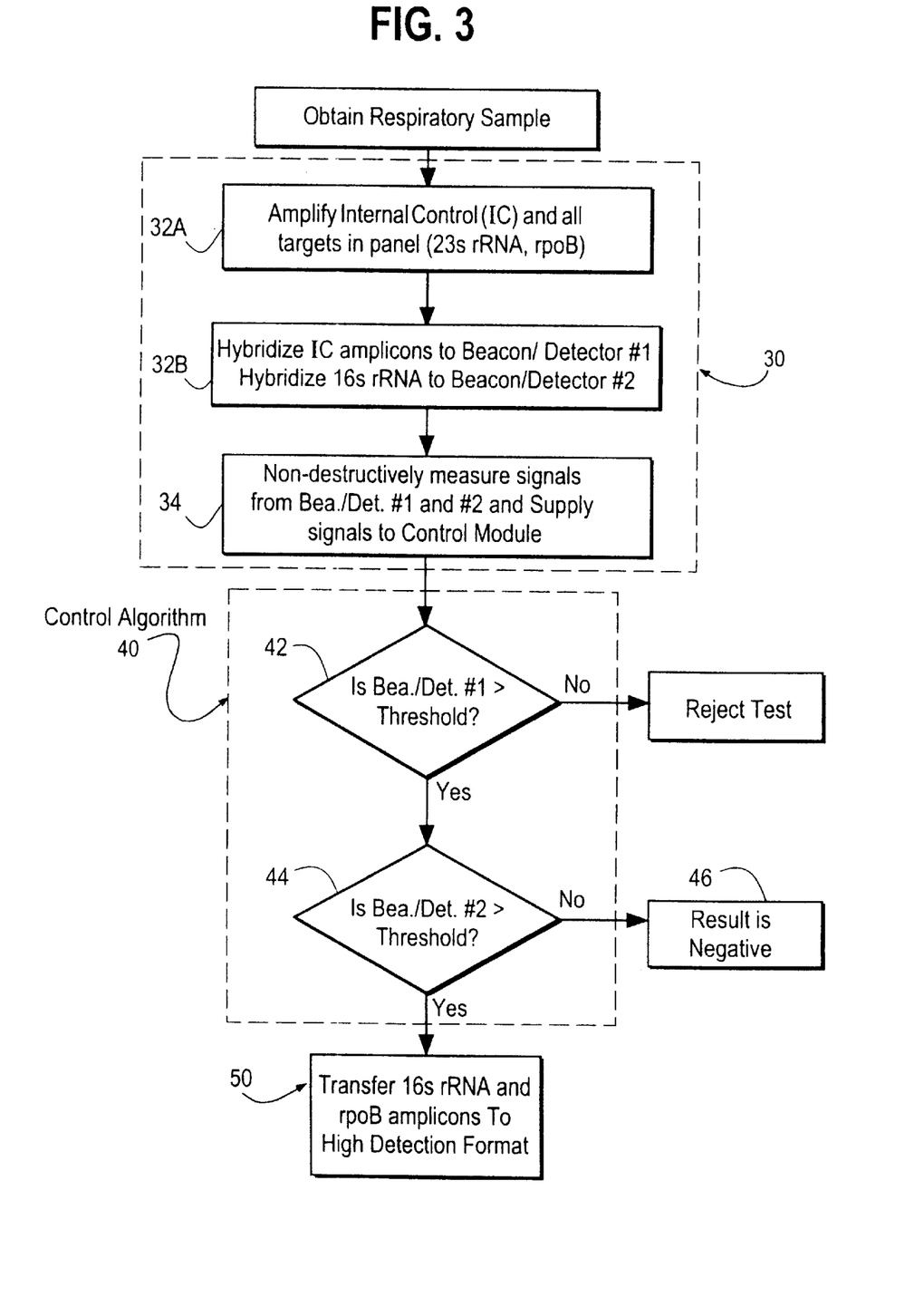
FIG. 3 illustrates a variation of the method of FIG. 2.

The first type of process in the preferred embodiment, a qualitative detection of the presence of a conserved region of the target, has been described above for testing of Mycobacterium organisms in sputum samples (see FIG. 3). For example, in FIG. 3 if the signal from the first hybridization reaction or the hybridization of the internal control amplicons to the first group of detectors or beacons/detectors is below the threshold level (step 42) the test is rejected. If the signal is above the threshold, the signal for the hybridization of the conserved 23S rRNA sequence to the second group of labeled or beacons/detectors is then analyzed at step 44. If this signal is below the threshold level, the control algorithm indicates that the result is negative, as indicated at 46. Conversely, if the signal is above the threshold level, then the amplicons, including other 23S rRNA amplified regions and rpoB are transferred to a high detection format as indicated at 50.

The second type of control process is also possible with the control algorithm: quantitative detection of one or more targets, to be used in conjunction with results of the multi-detection analysis. In some cases, the quantity of target nucleic acid is of analytical or diagnostic significance. As an example, consider an HIV patient being treated for AIDS. The measurement of total viral nucleic acid or viral load is an important diagnostic/therapeutic indicator. For example, if the viral load level is greater than a threshold, the clinician may benefit by further genotypic analysis of the HIV amplicons. Such analysis, which would require an expensive high detection format but may not be required if the total viral nucleic acid level is low with appropriate therapy. The main difference between this application and the simple qualitative example of FIG. 3 is that the quantitative signal is not only used in the control algorithm, but is also a reported result when accompanied and analyzed by data from known levels of virus; for example, in a multi-point calibration or when the level of internal control is known before amplification.

Figure 4:
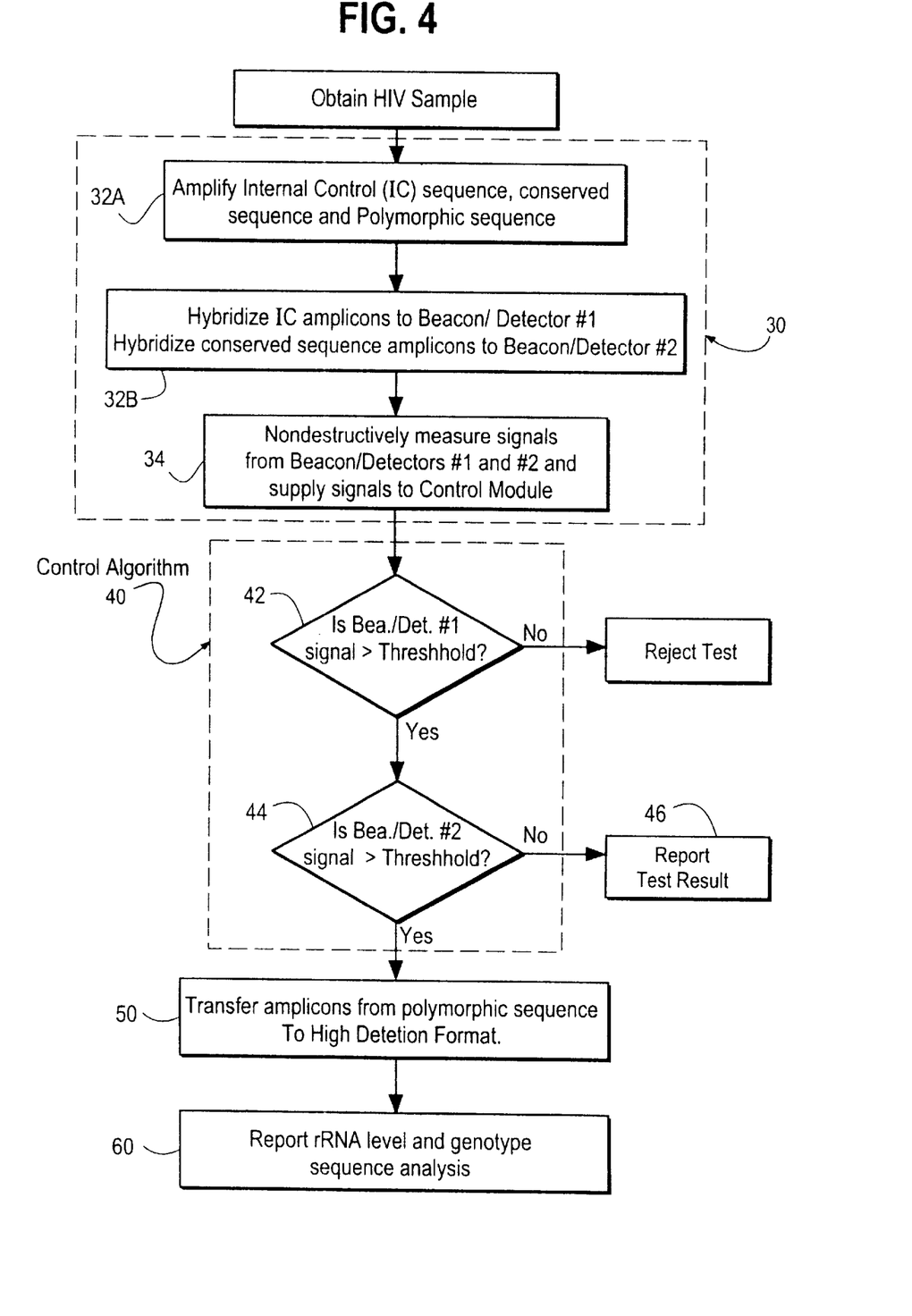
FIG. 4 illustrates a second embodiment of the method of FIG. 2, in which the control algorithm provides both a decision on whether to proceed with the second level of testing as well as a quantitative assessment of the level of nucleic acids in the sample.

An example of this second type of control algorithm is shown in FIG. 4. In this example, a sample is obtained from a patient with HIV. Step 30 (the low detection format) comprises the steps of amplifying the internal control sequence, a conserved HIV sequence and a polymorphic HIV sequence as indicated at step 32A. The process continues with the hybridization of the internal control amplicons to a beacons/detectors and the conserved sequence amplicons as indicated in step 32B. Alternatively, the amplicons are first captured to the solid support to form a complex and then detectors are hybridized to the complex for detection of amplicons. Next, the signals are measured from the hybridization of beacons/detectors complex as indicated in step 34. The resultant signals generated are digitized and sent to a control module or processing unit implementing the control algorithm 40.

In the control algorithm 40, the step 42 is the same as for FIG. 3. If the signal from the beacons/detectors #1 is less than the second threshold (step 44), the algorithm 40 provides a report for the nucleic acid which level is below the threshold for performing the high detection format as indicated at 46. In the event that the signal from the beacons/detectors #2 is greater than the second threshold, the amplicons are transferred to the second reaction station (step 50).

Alternatively, in a quantitative detection, the amplification of internal control (not shown) having known amounts of nucleic acid before amplification to separately obtain calibration data is submitted to the control algorithm. The result from signals detected at step 44 may be calculated against data derived from the internal control amplicons and reported as indicated at step 46.

The third type of process that may be implemented is a quantitative detection of one of several targets, and pre-selection of a specific panel of tests for the second hybridization reaction. As a more general case of one embodiment of FIG. 2, multiple beacons/detectors can be used to detect one or more of several possible targets to provide multiple input signals for use by the control algorithm. For example, a respiratory panel could be tested for Mycobacterium, Legionella, Mycoplasma, Influenza or RSV. Mycobacterium, because of the need to detect drug resistance in tuberculosis, is a complex target which may require a multi-detection analysis dedicated to this target alone. Similarly, Influenza and RSV are viruses and may each require a different multi-detection device. Thus, three different high detection formats may be appropriate for further or second analysis of the test sample. By choosing different conserved sequences for each of the three low detection formats, it is possible to design beacons/detectors that will allow the control algorithm to choose which one of the three high detection formats to select. An example of this third process is shown in FIG. 5.

Figure 5:
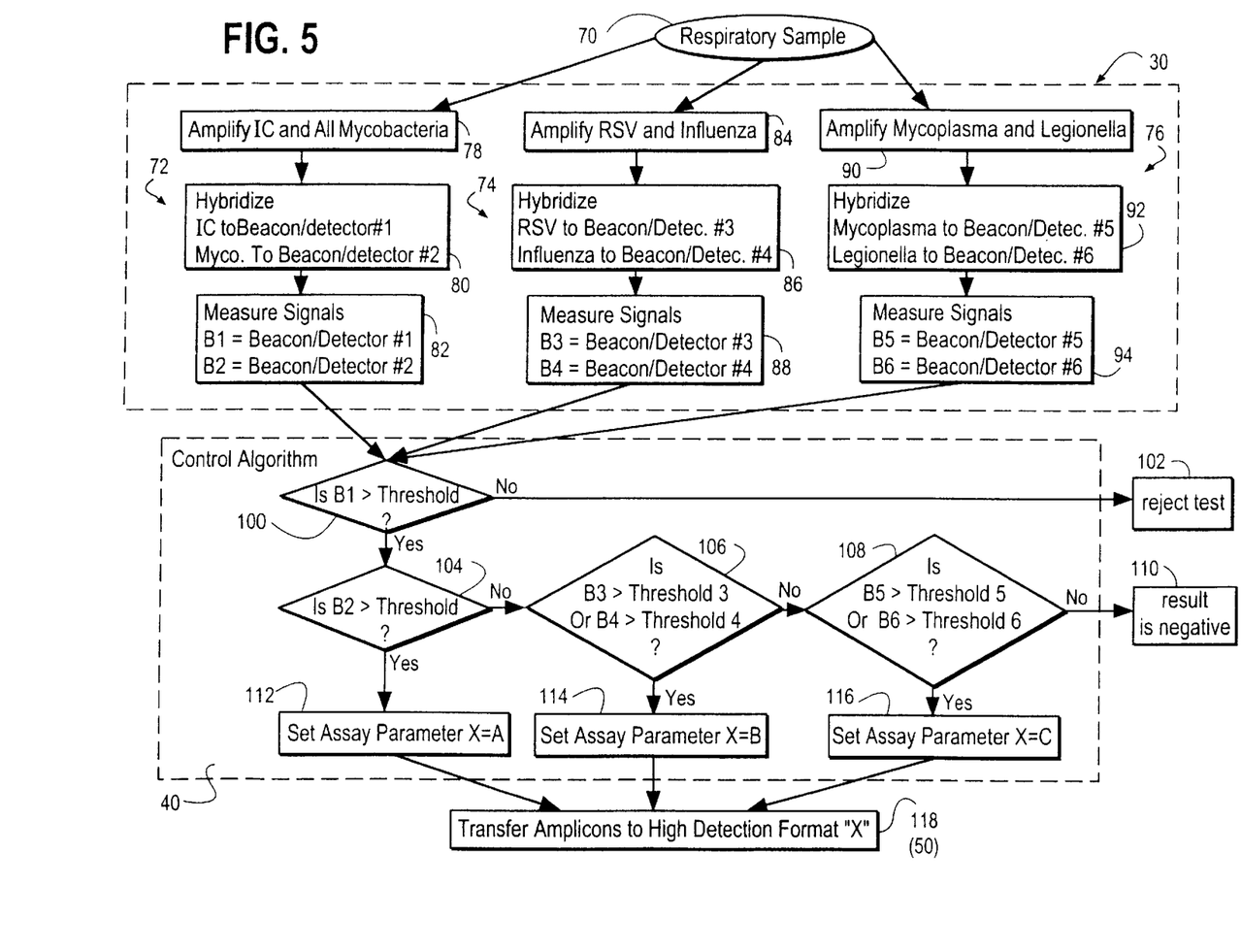
FIG. 5 illustrates a third embodiment of the method, in which three low detection formats are run in parallel, the signals representing the results are supplied to a control module for implementing a control algorithm. Three different assay parameters are supplied resulting in one input for selection of a single high detection format.

Referring now to FIG. 5, the basic features common to FIGS. 2 and 4 are also common to FIG. 5, namely the performance of the low detection format in step 30, using the signal outputs of the screen in a control algorithm 40, and controlling or initiating the more comprehensive high detection format assay in step 50 depending on the results of the control algorithm.

In the embodiment of FIG. 5, three low detection formats are run in parallel, as indicated 72, 74 and 76. In this example, a respiratory sample is obtained at step 70 for a given diagnostic hypothesis. The test sample is presented to the instrument and then treated to release nucleic acid. In the first format 72, the internal control is also amplified, along with all Mycobacteria RNA at step 78. The method continues at step 80 with the hybridization of the internal control amplicon to a first set of beacons/detectors and the Mycobacterium RNA amplicon to a second set of beacons/detectors. Finally, at step 82 the signals from the first and second sets of beacons/detectors are measured using known fluorescence or other type of detection equipment. The signals are converted to digital form and supplied to a control module, stand alone computer, or other processing station implementing the control algorithm 40.

For the second format 74, at step 84 the RSV and Influenza targets in the sample are amplified. The RSV and Influenza amplicons are hybridized to beacons/detectors designated numbers 3 and 4, respectively, at step 86. Then, the signals from the third and fourth sets of beacons/detectors are measured using known fluorescence or other type of detection equipment at step 88. The signals are converted to digital form and supplied to the control module implementing the control algorithm 40.

For the third format 76, at step 90 the Mycoplasma and Legionella targets in the sample are amplified. U.S. Pat. No. 5,614,388 describes methods for analyzing Legionella and is incorporated by reference herein. The amplicons are hybridized to beacons/detectors designated numbers 5 and 6, respectively, at step 92. Then, the signals from the fifth and sixth sets of beacons/detectors are measured using known fluorescence or other type of detection equipment. The signals are converted to digital form and supplied to the control module implementing the control algorithm 40. Internal control amplicons can be used to assess the amplification reaction and, if desired, for quantitative analysis.

The control algorithm in FIG. 5 first performs a comparison (indicated at step 100) of the internal control amplicon signal from the first format 72 to determine if the signal is greater than a predetermined threshold value. If not, the entire test is rejected as indicated at 102. If the internal control signal is greater than the threshold, the control algorithm proceeds to compare the second beacons/detectors signal (from format 72) to determine if it is greater than a second threshold. If it is greater than the second threshold, a positive result is indicated. A threshold value for a subsequent multi-detection assay is set, as indicated at 112. For example, at step 112 the positive result for the Mycobacterium in the respiratory sample indicates that a high detection format assay of type "A" should be initiated to further analyze Mycobacterium.

If the comparison at step 104 results in a negative value, the control algorithm still proceeds to determine if a negative result for the test as whole is warranted. Specifically, although the Mycobacteria result is negative, the control algorithm determines, at step 106, whether the measurement of the third beacon/detector signal is greater than the third threshold (for the RSV virus), or whether the measurement of the fourth beacon/detector signal is greater than the fourth threshold (for the Influenza virus). If either one of these beacons/detectors signals is greater than the threshold value, the algorithm 40 sets the assay parameter, x, to a second or different value or characteristic, e.g., "B", indicating a high detection format assay at type "B" should be initiated for further analysis of RSV or Influenza.

If the comparison at step 106 is negative, the algorithm proceeds to perform a similar analysis for the third format 76. Specifically, the control algorithm 40 determines, at step 108, whether the measurement of the fifth set of beacons/detectors signal is greater than the fifth threshold value (for Mycoplasma), or whether the measurement of the sixth set of beacons/detectors signal is greater than a sixth threshold value (for Legionella). If either one of these beacons/detectors signals is greater than the threshold value, the algorithm 40 sets the assay parameter, x, to a third or different value, e.g., "C" indicating an assay of type "C" should be initiated for further analysis of Mycoplasma or Legionella.

If the comparison at step 108 is negative, then all of the detectors/beacons in the three formats 72, 74, 76 (other than the control beacon) are negative. Therefore, the control algorithm indicates that a negative result has been obtained for the first screening test panel 30 and the instrument does not proceed with the high detection format.

Assuming that at least one of the comparisons at step 104, 106 and 108 results in a positive response, the appropriate amplicon(s) from formats having the positive results are transferred, preferably automatically to the appropriate high detection format. In a preferred embodiment, transfer steps from the first reaction station (30) to the second reaction station (50) occur without exposure of amplicons to the environment.

Persons skilled in the art will appreciate while three low format assays are run in parallel in FIG. 5, the process can be applied to any arbitrary number or combination of panels in the first step 30, and the control algorithm 40 modified to account for the different formats or combinations of formats with appropriate default settings.

Persons skilled in the art will also appreciate that the control algorithm 40 of FIG. 5 (as well as for the other figures) could be implemented in hardware using, for example logic gates. However, since the reaction stations of the instruments performing either screening analysis 30 or multi-detection analysis 50 would be expected to be linked to a programmable central processing unit, it would be preferable to have the control module implemented in the processing unit rather than constructing a discrete hardware control module. However, given the operation steps of the control algorithm in FIGS. 2–5, a control module implemented entirely in hardware would certainly be another embodiment Referring now to FIG. 6, an instrument 120 for performing the methods of FIGS. 2–5 shown in block-diagram form provides a combination of modules, the method of operation and communication thereof as described herein.

Figure 6:
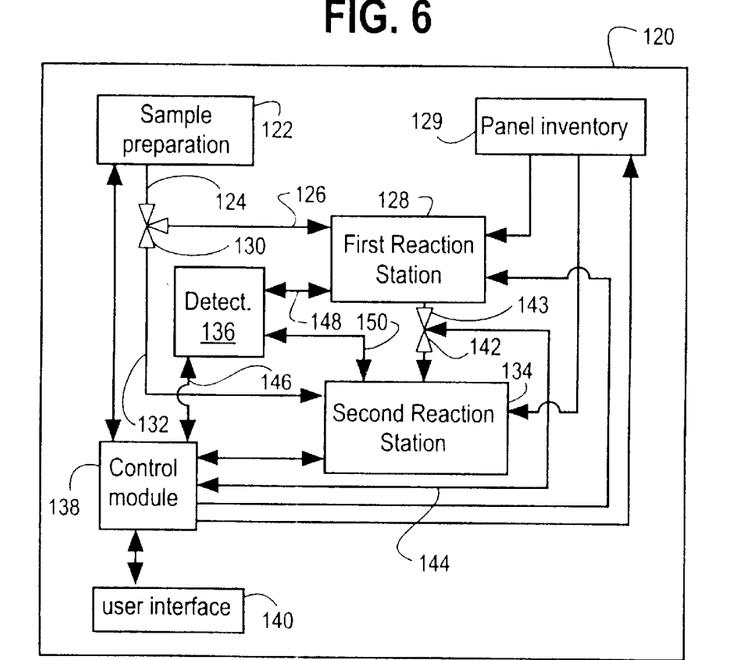
FIG. 6 is a block diagram of a preferred analytical instrument for use in performing the methods of FIGS. 2–5.

Referring to FIG. 6, sample is transferred between the sample preparation station 122, to first 128 and second 134 reaction stations (when necessary) of the instrument through a fluidic transfer means, for example a passageway 124, 126, 132. Alternatively, amplicons can be transferred from the first reaction station 128 to the second reaction station 134 through fluid passageway 142 controlled by control module 138. The transfer is made automatically without human intervention and without contact between liquids and the external environment which minimizes the risk of sample contamination and release of airborne amplicons from the amplification reaction.

Transfer of sample from the sample processing station 122 to the first 128 and second 134 reaction stations to the detection station 136 can be effected without actually moving the sample in fluidic passageways 124, 126, 132. Transfer can also be effected from the first reaction station 128 to the second reaction station 134 where a high detection format is performed. This can be done through chambered sample modules such as that described in U.S. Pat. No. 5,786,182 (Catanzariti). Such chambers may also be the site of sample preparation steps. Another example of a means to effect such transfer is described in FR 9811383 filed Sep. 8, 1998.

As noted above, the station 128 in FIG. 6 performs a first set of hybridization reactions. The first reaction station 128 incorporates a medium or device having a means for analyzing at least one to ten discrete nucleic acid sequences suspected of being present in the test sample. The internal control amplicons can also be detected and, therefore, probes complementary to the internal control amplicons must also be provided.

The instrument 120 includes at least one suitable detection system 136 and a control module 138 that are used in determining a positive hybridization signals of the target or amplicons in the first hybridization reaction. More particularly, the detection system 136 provides signals to the control module 138, which are then digitized for use by a central processing unit in the control module 138 to perform the control algorithm 40 of FIGS. 2–5.

The second reaction station 134, in a preferred embodiment, comprises a station for performing a second set of hybridization reactions on a high detection format device retrieved from the inventory 129. The high detection format comprises a medium or device having means for analyzing greater than one hundred discrete nucleic acid sequences and typically four hundred discrete nucleic acid sequences and preferably greater than one thousand discrete nucleic acid sequences. The high detection format is an example of the multi-detection assay described earlier.

The control module 138 provides integration and control over the entire operation of the instrument 120. The control module 138 determines the need for completion or implementation of the second set of hybridization reactions on one or more selected high detection formats based on whether a positive hybridization of the target or amplicons in the first low detection format was detected by detector station 136, as described in FIGS. 2–5. Finally, the detector station 136 and control module 138 detect positive hybridization signals of a plurality of target or amplicons on the high detection format in station 134, wherein the high detection format provides further analytical data for the target nucleic acid sequence in the test sample.

The instrument 120 includes a sample processing station 122. The investigator places a biological or analytical sample, e.g., from a human patient or other source in the station 122, wherein the sample is processed in accordance with techniques either known in the art or described herein. The station 122 preferably includes an integral amplification station component to amplify nucleic acids in the event that sample source or other circumstances dictate that amplification is advisable. The amplification station may also be a separate station. Additionally, in an alternative embodiment, amplification of the sample could be initiated if the detection station 136 indicates that a non-amplified sample result is negative. Specific sample processing steps will be determined in part by the sample analysis being performed.

The instrument 120 includes a fluidic transfer means, for example, fluid passageway or conduit 124 connected to the sample processing station 122 that supplies a fluid containing the target or amplicons to a three-way valve 130. The valve 130 can be controlled by the control module 138 to supply the fluid to a second conduit 126 leading to a first reaction station or module 138, wherein the low detection format (step 30 in FIGS. 2–5) is performed. In the event that a fluid conduit 124 is chosen as the means to supply the sample to the first reaction station 128, suitable and conventional decontamination/cleaning processes should be used for the conduit 124 to prevent sample contamination. Examples include acid, bleach, ozone, or other chemical techniques, thermal or electrical techniques.

The first reaction station 128 performs the hybridization reaction with the targets or amplicons, signals from the detector probes are made by a detection station 136. The detection station 136 measures the signals (e.g., fluorescence or luminescence) from the detector probes complementary to the target amplicons, digitizes the signals, and supplies them along a digital data bus 146 to the control module 138.

The control algorithm 40 described herein is performed either in hardware or in software in the control module 138.

In a preferred embodiment, the screening assay used in the first reaction station 128 is performed in a disposable device, and is selectable by the instrument 120 based on inputs from the user at the user interface 140. For example, if the user is processing a blood specimen from a patient, or throat specimen, for each type of sample the instrument 120 will use a different type of low detection format in the station 128. The user would input the type of patient sample at the user interface 140 and the control module selects a panel for the low detection format from an inventory 129 of panels or otherwise instructs the user to load such disposables into the instrument system. Ideally, to lower the cost for tests using low detection formats test in the first reaction station 128, the device would comprise panels having a limited number of wells or chambers to detect a small spectrum of agents. (e.g., ten or less wells, perhaps more, depending on the source of the sample). Furthermore, all the different types of formats stored in the inventory 129 should be labeled with bar codes or similar indicia so that the identification of the panel can be confirmed by safety processing routines in the instrument 120 and that the correct format can be retrieved from the inventory 129.

The first reaction station 128 is positioned in close proximity to a detector station 136. The detector station 136 contains for example a photomultiplier tube, fluorescence detector, or other type of detection system depending on the type of signal to be detected in the first reaction station 128. The devices containing the assay in the first reaction station 128 could also be moved by suitable translation mechanisms to the detector station 136. A preferred detection label is chemiluminescence or fluorescence.

Depending on the results of the control algorithm implemented in the control module 138, the test is either rejected, deemed to be negative, or processed in the multi-detection assay. One example of how this could proceed is to have the control module 138 issue an analog signal along conductor 144 to a valve 142 placed in a conduit linking the first reaction station 128 to a second reaction station 134 in which the high detection format is performed. When the valve 142 opens, a fluid containing the amplicons for the target under test are transferred to the second reaction station 134.

In a representative embodiment, the hybridization reaction in the second reaction station 134 is provided on a disposable high detection device, such as a high density array product similar to that described above. The high detection format for use in the second multi-detection analysis is likewise retrieved from the device inventory 129. Multiple detection means may be further incorporated in or adjacent to the second reaction station 134 to detect hybridizations in the high detection format.

When the detection station 136 has finished with the detection of the hybridization signals from the second reaction station, the results are processed in the control module 138 and displayed at the user interface 140. Alternatively, the instrument 120 could prepare and print out a suitable report, store the data electronically for subsequent retrieval, or send the data or results to additional instruments or computer locations.

Figure 7:
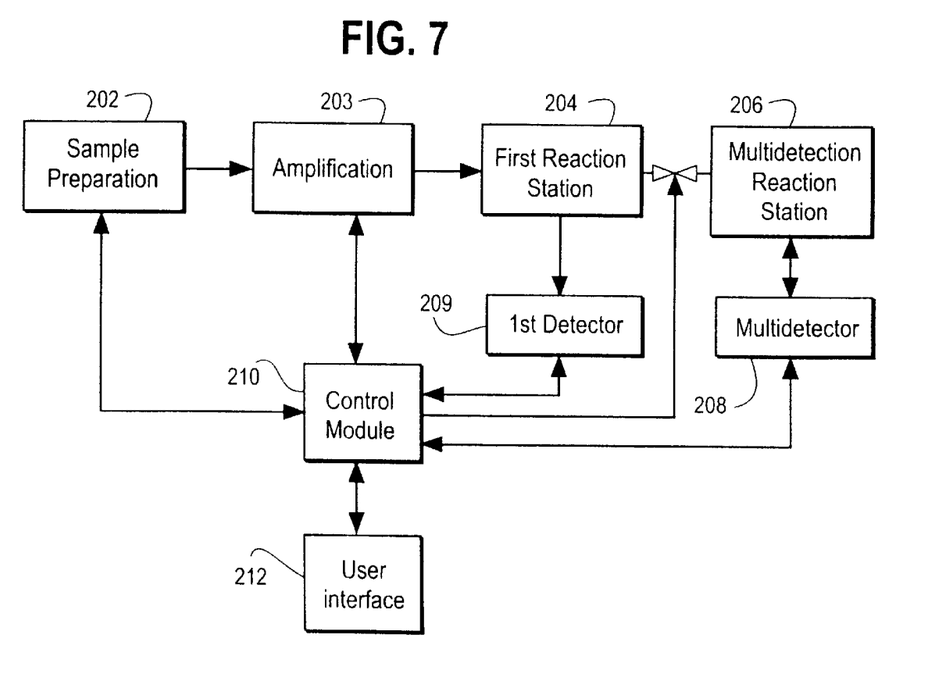
FIG. 7 is a block diagram of an alternative design of an analytical instrument for performing the method of FIGS. 2–5.

Referring now to FIG. 7, another design of an analytical instrument 200 for performing the method of FIGS. 2–5 is shown in block diagram form. The instrument 200 has the same basic organization and operation as the instrument of FIG. 6. The instrument has a sample preparation station 202 and amplification station 203 for processing and then amplifying nucleic acid sequences in test samples as explained herein. The station provides amplicons to a first reaction station 204 where a device is processed to effect hybridization of the target and internal control amplicons in the sample to the beacons/detectors. The panel or devices processed in station 204 is positioned in proximity to a detector 209, which makes measurements of the hybridization product and provides signals to the control module 210. The control module 210 implements the algorithm 40 from FIGS. 2–5. A detector module 208 is positioned in close proximity to the second reaction station 206. The high detection format or other device is used in the second reaction station 206 and read by the detector module 208 and the signals are provided to the control module 210 in the manner explained herein. The control module 210 only directs transfer of amplicons from the first reaction station 204 to the second reaction station 206 if the results of the control algorithm indicate that the high detection format assay is warranted. Final results are either displayed on a user interface 212, printed out on a report, or transferred electronically as needed.

As noted previously, the control algorithm provides a means to determine whether to direct transfer of amplicons to a selected high detection format assay from the first reaction station 204. The second reaction station should physically be separated from the first reaction station so that its use is completely optional. In the first part of the test (i.e., step 30 in FIGS. 2–5), the amplification processing step 30 can generate large quantities of amplicons which must be contained or they become potential contaminants for future tests. One normally would try to keep this part of the test processing station sealed or confined in some manner, because of the requirement to limit potential contamination during transfer of these amplicons physically to test modules.

In another aspect, the system preferably includes a fluidic passageway to transfer the target, preferably amplicons, from a supply or other source to the first reaction station, and if directed, amplicons to a second reaction station, as determined by said control module, without human intervention.

Alternatively, a transfer device may receive amplicons and be transferred to the first reaction station and as necessary to a second reaction station for transfer of amplicons to one or more second reaction stations 206.

EXAMPLES

The following examples serve to describe various embodiments of the present invention. The examples shall not be construed as limiting the invention to these embodiments but are defined solely by the claims concluding this specification and equivalents thereof.

Example 1

Amplification of a conserved region of Mycobacteria is performed from a test sample in a first test reaction station. Nucleic acid sequences are described in U.S. Pat. No. 5,547,842 (Hogan); U.S. Pat. No. 5,643,723 (Persing); U.S. Pat. No. 5,589,585 (Mabilat); U.S. Pat. No. 5,702,317 (Mabilat), and U.S. Pat. No. 5,849,901 (Mabilat).

For isolates, one or two freshly grown colonies of bacteria (3–5 mm diameter ca $10^8$ bacteria) were scraped on the end of a spatula and resuspended in 250 µl of sterile water in a 1.5 ml Eppendorf tube. Total nucleic acids were released from culture material by vortexing the bacterial suspension in the presence of glass beads. A 5 µl aliquot of the lysate was added directly to the PCR reaction. Alternatively, 20 ng of plasmid DNA was added to the PCR reaction. The 16S hypervariable region was PCR-amplified using Mycobacterium genus primers (positions 213–236 and 394–415 on the M. tuberculosis reference sequence, M20940, Genbank, TB amplicon size is 202 bp). The primers also contained either a bacteriophage T3 or T7 promoter sequence at their 5' end: T3-M1 (SEQ ID NO: 1) 5'aattaaccctcactaaagggAA-CACGTGGGTGATCTGCCCTGCA and T7-M2 (SEQ ID NO: 2) 5'-(SEQ ID NO: 2)gtaatacgactcactatagggctTGTGGCCGGACACCCTCTCA (promoter sequences in lowercase letter, mycobacteria sequence in uppercase letter). The M. tuberculosis rpoB Rif locus was amplified using MTX 2281 TB and MTX 2985 TB primers, described above, and tailed with T3 or T7 promoter sequences. Amplification of the M tuberculosis katG region analyzed on the array was performed using T3 or T7-tailed primers 33f (SEQ ID NO: 3) 5'-TCACAGCCCGATAACACCAAC and 2288r 5'-GGCCGATCAACCCGAATCAGC (positions 1942–1962 and 4197–4217 on X68081, TB amplicon size is 2275 bp).

PCR was carried out in a 100 µl reaction volume containing 50 mM KCl, 10 mM Tris, pH 8.3, 1.5 mM $MgCl_2$, 0.001% (w/v) gelatin, 5% (v/v) DMSO, 0.5 µM of each primer, 200 µM of each of the four deoxynucleotide triphosphates and 1.5 unites of Taq polymerase (AmpliTaq, Perkin-Elmer). PCR was performed in a Perkin-Elmer 2400 thermal cycler with an initial denaturation step at 94° C. for 5 min and cycling conditions at 94° C. for 45 sec. 60° C. for 30 sec, 72° C. for 30 sec (2 min for katG target) for 35 cycles and 72° C. for 10 min for the last cycle.

In order to screen if Mycobacteria is present in a sample, a probe, designed in a conserved region of Mycobacteria, such region being amplified by the two primers, must be prepared. In this example, a detection probe (SEQ ID NO: 4) comprising the sequence 5' GATGAGCCCGCGGC-CTATCAGCTTGTTGGT 3' allows the screening. After denaturation of the PCR fragment by heat or alkaline treatment, hybridization of the amplified fragment to the labeled probe (as described in Nucleic Acids Research, Vol. 26, pp 2150–2155 (1998) the analysis of the fluorescent signal indicates Mycobacteria species are present in the sample.

When the screening procedure was positive, the promoter-tagged PCR amplicons were used for generating labeled single-stranded RNA targets in vitro transcription. Each 20 µl reaction contained approximately 50 ng of PCR product, 20 U of T3 or T7 RNA polymerase (Promega), 40 mM Tris Acetate, pH 8.1, 100 mM Mg(acetate)$_2$, 10 mM DTT, 1.25 mM each ATP, CTP and GTP, 0.5 mM UTP and 0.25 mM fluorescein-UTP. The reaction was carried out at 37° C. for 1 hour. In vitro transcribed RNA was fragmented either by adjusting the concentration of $MgCl_2$ to 30 mM and heating at 94° C. for 30 min or by incubation with 30 mM $MnCl_2$ and 30 mM immidazole at 65° C. for 30 min. The efficiency of fragmentation was analyzed by denaturing PAGE.

An array tiling strategy similar to that described in U.S. Pat. No. 5,837,832 (Chee) was used to identify the sequences differentiating the Mycobacterium species and the rpoB mutations. For every base within a given reference sequence, four probes of equal length are synthesized on the array. The interrogated base is centrally located within the probes, which also have common 3' and 5' termini. One probe is an exact complement to the reference sequence, while the three other probes represent the possible single base mismatches to the interrogated base. Base cells are determined by comparing the hybridization intensity of a labeled target to the four probes. For the 16S rRNA sequences, probe redundancy was eliminated by synthesizing probes shared by two or more referenced only once on the array. In addition to the wild-type probes for rpoB, each rifampin-resistance mutation is represented by its own set of probes. The array also contains 2.2 kb of the M tuberculosis katG gene sequence, which encodes catalase peroxidase. The probe array is divided into four distinct zones corresponding to 16S rRNA, rpoB antisense, rpoB sense and katG sense sequences. The array is divided into specific 50 μm×50 μm units or cells over a 1.28 cm×1.28 cm area, making a total number of 65,000 different synthesis sites. A database of 82 unique 16S rRNA sequences was utilized to design the array, which enables the discrimination of 54 phenotypically distinct species. Certain species or taxonomic complexes are represented by more than one reference sequence due to the sequence heterogeneity observed in the region of the 16S rRNA tiled on the array (i.e., the M avium-intracellulare complex). Also a database of rpoB sequences from 61 rifampin-resistant isolates is represented on the array. Those sequences contain 51 unique rpoB mutations.

Hybridization of the probe arrays were performed using the GENE CHIP Fluidics Station (Affymetrix). One to 5 μl of the fragmented labeled RNA target were diluted in 500 μl of hybridization buffer. Hybridization buffer 1 consisted of 4.5×SSPE (0.675M NaCl, 45 mM NaH$_2$PO$_4$, 4.5 mM EDTA, pH 7.4). 0.005% (v/v) Triton X-100 at 30 C. Fluorescent signal emitted by target bound to the array was detected at a density of 6 by using the GeneArray Scanner (Hewlett Packard, Palo Alto, Calif.). Probe array cell intensities, nucleotide base-call, sequence determination and reports were generated by functions available on GENE CHIP software (Affymetrix). A candidate selection index was determined by the percent of homology between the experimentally derived sequence and all of the reference sequences tiled on the array. Nucleic acid sequences are described in U.S. Pat. No. 5,589,585 (Mabilat); U.S. Pat. No. 5,702,317 (Mabilat), and U.S. Pat. No. 5,849,901 (Mabilat) or are available on Genbank or other databases.

Example 2

HIV Analysis

HIV nucleic acid sequences used in the first arrays of the invention and specifically for viral load determination have been published in Lin, et al., J Clin. Microbiol. 36(3), pp. 835–839 (1998) and Korber, et al., Science 280, pp 1868–1871 (1998) or are available to the public on Genbank or other databases. Published documents which describe HIV nucleic acid sequences include EP 0 345 375 (De Leys); EP 0 173529 (Wong-Staal); EP 0 178978 (Alizon); EP 0 181150 (Luciw) and EP 0 185444 (Chang). U.S. Patents describing nucleic acid sequences include U.S. Pat. No. 5,079,342 (Alizon) and U.S. Pat. No. 5,310,541 (Alizon). See also Kozal, Michael J. et al., "Extensive polymorphisms observed in HIV-1 clade B protease gene using high-density oligonucleotide arrays", Nature Medicine, Vol. 2, no. 7, pp. 753–759 (July 1996).

I claim:

1. A method for performing nucleic acid sequence analysis, the method performed in an automated nucleic acid testing instrument providing a first detection format, and where indicated from the results of said first detection format, a second detection format under control by a control module associated with said instrument, comprising the steps of:
   (a) conducting a first hybridization reaction with at least one target nucleic acid sequence or its complementary sequence from a test sample, said first hybridization reaction performed in said first detection format;
   said first detection format comprising one to fifty known nucleic acid sequences;
   (b) generating a signal from said first hybridization reaction;
   (c) supplying said signal to said control module,
   (d) processing said signal in said control module to determine whether said signal is greater than a threshold level;
   (e) in the event that said signal is greater than said threshold level, automatically where further data analysis is required, transferring said target nucleic acid sequences or their complementary sequences to second said high detection format device in said instrument;
   said second detection format comprising greater than one hundred known nucleic acid sequences;
   (f) conducting a second hybridization reaction in said second detection format device;
   (g) generating a signal from said second reaction; and
   (h) processing said signal in said control module to analyze data pertaining to said target nucleic acid sequences.

2. The method of claim 1, wherein said second reaction comprises a second detection format comprising greater than one thousand nucleic acid sequences.

3. The method of claim 1, further comprising the steps of simultaneously amplifying selected target nucleic acid sequences and internal control nucleic acid sequence, measuring a signal from said internal control, comparing said internal control signal with a threshold value for said internal control, and rejecting said test in the event that said internal control signal is less then said internal control threshold value.

4. A method for conducting a nucleic acid analysis in an automated nucleic acid testing instrument, comprising the steps of:
   amplifying all target nucleic acid sequences in a test sample and internal control sequences which are needed for both screening and multi-detection analysis;
   performing a first analysis of one or more amplified nucleic acid sequences;
   wherein said first analysis uses a first detection format having one to fifty known nucleic acid sequences;
   measuring internal control signals and target signals from said first analysis;
   supplying said internal control signals and said target signals to a control module;
   implementing a control algorithm in said control module, said algorithm:
      i) comparing said internal control signals with a first threshold value, said comparison determining whether to reject said test; and if said comparison indicates that said test is not rejected; and
      ii) comparing said target signals with a second threshold; and where further data analysis is required:
   transferring said one or more previously amplified nucleic acid sequences to a second device and conducting said second analysis in said device in response to an output of said control algorithm and wherein said second device comprises a second format having greater than one hundred known nucleic acid sequences.

5. The method of claim 4, wherein each of said steps are performed automatically and without human intervention by an integrated nucleic acid testing instrument.

6. A diagnostic method for data collection from a test sample containing one or more nucleic acid sequences, the method performed by an automated instrument comprising:

a. releasing nucleic acid sequences from a test sample;
b. amplifying said nucleic acid sequences to produce amplicons;
c. providing said amplicons to a first detection format comprising one to fifty complementary nucleic acid sequences to one or more of said amplicons for a hybridization reaction;
d. detecting the presence of said amplicons hybridized by said first detection format; and
e. determining by means of a control algorithm a positive or negative result in step c, wherein said amplicons from step b are further analyzed in a second detection format having greater than one hundred known nucleic acid sequences for data collection if a positive result has been obtained and if further data analysis is required.

7. The method of claim 1 wherein an amplification process is performed on said target nucleic acid or its complementary sequence either before or after the performing of step (a).

8. The method of claim 1, wherein said first format comprises between one and ten known nucleic acid sequences.

9. The method of claim 4, wherein said first detection format comprises between one and ten known nucleic acid sequences.

10. The method of claim 6, wherein said first detection format comprises between one and ten known nucleic acid sequences.

* * * * *

UNITED STATES PATENT AND TRADEMARK OFFICE
CERTIFICATE OF CORRECTION

PATENT NO.   : 6,225,067 B1
DATED        : May 1, 2001
INVENTOR(S)  : Charles Rogers It is certified that error appears in the above-identified patent and that said Letters Patent is hereby corrected as shown below:

<u>Column 19,</u>
Lines 53-54, in part (e) of claim 1: after the phrase "their complementary sequences to", delete the phrase "second said high" and insert in its place -- said second --.

Signed and Sealed this

Twenty-seventh Day of November, 2001

*Attest:*

NICHOLAS P. GODICI
*Attesting Officer*          *Acting Director of the United States Patent and Trademark Office*